US008603447B2

(12) United States Patent
Mueller et al.

(10) Patent No.: US 8,603,447 B2
(45) Date of Patent: Dec. 10, 2013

(54) AGENT FOR TREATING KERATIN-CONTAINING FIBERS, CONTAINING A NON-IONIC STARCH MODIFIED BY PROPYLENE OXIDE AND AN ADDITIONAL FILM-FORMING AND/OR STABILIZING NONIONIC POLYMER

(75) Inventors: Burkhard Mueller, Hamburg (DE); Pamela Kaftan, Hamburg (DE); Rolf Bayersdoerfer, Hamburg (DE); Matthias Schweinsberg, Hamburg (DE); Ralf Roenisch, Wuppertal (DE); Mathias Schriefers, Moenchengladbach (DE); Carine Dogan, Vigneux sur Seine (FR); Thorsten Knappe, Schenefeld (DE); Miriam Reineking, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/453,015

(22) Filed: Apr. 23, 2012

(65) Prior Publication Data

US 2012/0207692 A1    Aug. 16, 2012

Related U.S. Application Data

(63) Continuation of application No. PCT/EP2010/065859, filed on Oct. 21, 2010.

(30) Foreign Application Priority Data

Oct. 22, 2009 (DE) .......................... 10 2009 045 925
Oct. 22, 2009 (DE) .......................... 10 2009 045 933

(51) Int. Cl.
*A61K 8/72* (2006.01)

(52) U.S. Cl.
USPC .................................... 424/70.11; 424/70.31

(58) Field of Classification Search
None
See application file for complete search history.

(56) References Cited

U.S. PATENT DOCUMENTS

| 4,528,283 A | 7/1985 | Lang et al. |
| 4,780,310 A | 10/1988 | Lang et al. |
| 4,976,952 A | 12/1990 | Lang et al. |
| 5,520,200 A | 5/1996 | Sturla |
| 6,235,913 B1 | 5/2001 | Raths et al. |
| 6,344,183 B2 * | 2/2002 | Paul et al. ....................... 424/47 |
| 7,332,466 B2 | 2/2008 | Schmid et al. |

FOREIGN PATENT DOCUMENTS

| AU | 730455 B2 | 3/2001 |
| DE | 19756454 C1 | 6/1999 |
| DE | 10352470 A1 | 6/2005 |
| EP | 0274086 A2 | 7/1988 |
| EP | 0580514 A1 | 1/1994 |
| EP | 0948958 A2 * | 4/1999 |
| EP | 0984960 A2 * | 4/1999 |
| EP | 0948958 A2 | 10/1999 |
| EP | 0948959 A2 | 10/1999 |
| EP | 0948960 A2 | 10/1999 |
| EP | 1317916 A2 | 6/2003 |
| WO | 02083089 A1 | 10/2002 |

OTHER PUBLICATIONS

Reiger, Martin, Harrys Cosmeticology, vols. I-II, Chemical Publishing Company, Inc. Chapter 30, pp. 635-667, 2000.*
International Cosmetic Ingredient Dictionary & Handbook. The Cosmetic Toiletry and Fragrance Association, 7th Edition, 1997.
Gottschalck, T.E. et al. "International Cosmetic Ingredient Dictionary and Handbook." The Cosmetic, Toiletry and Fragrance Association, 12th Edition, vol. 3, 2008, pp. 3187-3192 and 3214-3215, XP002627782.

* cited by examiner

*Primary Examiner* — Anand Desai
*Assistant Examiner* — Melissa Mercier
(74) *Attorney, Agent, or Firm* — Krista A. Kostiew; David LeCroy

(57) ABSTRACT

Agent for treating keratin-containing fibers, particularly human hair, comprising, in a cosmetically acceptable carrier, (a) at least one nonionic starch modified with propylene oxide, and (b) at least one additional nonionic film-forming and/or nonionic setting polymer containing at least one structural unit chosen from the structural units of formulae (M1) to (M6), wherein R is a hydrogen atom or a methyl group, R' is a hydrogen atom or a ($C_1$ to $C_4$) acyl group, R" and R"" are, mutually independently, a ($C_1$ to $C_7$) alkyl group or a hydrogen atom, R'" is a linear or branched ($C_1$ to $C_4$) alkyl group or a ($C_2$ to $C_4$) hydroxyalkyl group; use of the agents for temporary deformation of hair and for hair care, particularly as an aerosol hair spray or aerosol hair foam.

15 Claims, No Drawings

AGENT FOR TREATING KERATIN-CONTAINING FIBERS, CONTAINING A NON-IONIC STARCH MODIFIED BY PROPYLENE OXIDE AND AN ADDITIONAL FILM-FORMING AND/OR STABILIZING NONIONIC POLYMER

CROSS REFERENCE TO RELATED APPLICATIONS

The present application is a continuation of International Application No. PCT/EP2010/065859 filed 21 Oct. 2010, which claims priority to German Patent Application Nos. 10 2009 045 925.1 and 10 2009 045 933.2, both filed 22 Oct. 2009, each of which are incorporated herein by reference.

The present invention relates to agents for hair treatment containing a combination of at least one nonionic starch modified with propylene oxide, and at least one nonionic film-forming and/or setting polymer; use of those agents for temporary deformation and/or care of keratin-containing fibers; and to aerosol hair sprays/foams based on those agents.

"Keratin-containing fibers" refers to all animal hairs (e.g., wool, horsehair, angora hair, furs, feathers, and products or textiles fabricated therefrom). Keratinic fibers are, however, preferably human hair.

Hair treatment agents that provide permanent or temporary shaping of hair play an important role in cosmetics. Temporary shaping actions that yield good hold without impairing the hair's healthy appearance such as its shine can be achieved, for example, using hair sprays, hair waxes, hair gels, hair foams, blow-dry waves, etc.

Corresponding agents for temporary shaping usually contain synthetic polymers as a shaping component. Preparations that contain a dissolved or dispersed polymer can be applied onto hair using propellant gases or a pump mechanism. Hair gels and hair waxes in particular, however, are generally not applied directly onto the hair but rather distributed in the hair by a comb or the hands.

An important property of an agent for temporary deformation of keratinic fibers, hereinafter also called a "styling agent", is to impart the strongest possible hold to the treated fibers in the shape that is generated. If the keratinic fibers involved are human hairs, terms also used are strong "hairstyle hold" or high "degree of hold" of the styling agent. Hairstyle hold is determined substantially by the nature and quantity of the synthetic polymer used, although further ingredients of the styling agent can also have an influence.

In addition to a high degree of hold, styling agents must also meet an additional large number of requirements. These can be divided roughly into properties on the hair; properties of the particular formulation (e.g., properties of the foam, gel, or sprayed aerosol); and properties relating to handling of the styling agent, with properties on the hair being particularly important. These include moisture resistance, low tack, and a balanced conditioning effect. In addition, if possible, a styling agent should be universally usable for all types of hair.

A variety of synthetic polymers used in styling agents have already been developed in order to meet these different requirements. These polymers can be divided into cationic, anionic, nonionic, and amphoteric film-forming and/or setting polymers. Ideally, upon application to hair the polymers yield a polymer film that provides a strong hold to the hairstyle while is sufficiently flexible so not to break under stress. If the polymer is too fragile, this results in formation of "film plaques" (i.e., residues that detach as the hair moves and gives the impression that the user of the corresponding styling agent has dandruff).

It is still difficult to develop styling agents that provide all desired properties in combination. This particularly applies to the combination of strong hold and simple, uniform application onto the keratin-containing fibers.

The present invention therefore provides an agent for temporary deformation and/or care of keratinic fibers that is notable for a high degree of hold and/or an excellent care-providing effect, and particularly has outstanding ease of handling during application onto the keratin-containing fibers.

It has now been surprisingly found that this can be achieved by a combination of specific polymers. It has further been possible in specific embodiments of the invention to provide, in addition to these outstanding properties, compositions without turbidity. Freedom from turbidity is significant particularly in the provision of aerosol compositions, since solid suspended particles can clog the exit nozzle of the aerosol package. For turbid and low-viscosity compositions, a general risk of sedimentation additionally exists, which has a disadvantageous effect on shelf stability of the composition.

A first subject of the present invention is therefore an agent for treating keratin-containing fibers, particularly human hair, containing, in a cosmetically acceptable carrier, (a) at least one nonionic starch modified with propylene oxide, and (b) at least one additional nonionic film-forming and/or nonionic setting polymer containing at least one structural unit chosen from the structural units of formulae (M1) to (M6),

(M1)

(M2)

(M3)

(M4)

(M5)

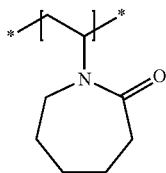

(M6)

wherein
R is a hydrogen atom or a methyl group,
R' is a hydrogen atom or a ($C_1$ to $C_4$) acyl group,
R" and R"" are, mutually independently, a ($C_1$ to $C_7$) alkyl group or a hydrogen atom,
R'" is a linear or branched ($C_1$ to $C_4$) alkyl group or a ($C_2$ to $C_4$) hydroxyalkyl group.

"Film-forming polymers" are those polymers that, upon drying, leave behind a continuous film on the skin, hair, or nails. Film-formers of this kind can be used in a very wide variety of cosmetic products such as, for example, face masks, make-up, hair setting agents, hair sprays, hair gels, hair waxes, hair therapies, shampoos, or nail polishes. Those polymers having sufficient solubility in water, alcohol or in water/alcohol mixtures to be present in the agent according to the present invention in completely dissolved form are particularly preferred. The film-forming polymers can be of synthetic or natural origin.

"Film-forming polymers" are also according to the present invention those polymers that, when applied in a 0.01- to 20-wt % aqueous, alcoholic, or aqueous alcoholic solution, are capable of depositing a transparent polymer film on the hair.

Setting polymers contribute to hold and/or buildup of hair volume and hair fullness of the overall hairstyle. These polymers are at the same time also film-forming polymers and are therefore generally typical substances for shape-imparting hair-treatment agents such as hair setting agents, hair foams, hair waxes, and hair sprays. It is certainly possible for film formation to be localized, and for only a few fibers to be connected to one another.

The "curl retention" test is often used as a test method for the setting effect of a polymer.

In accordance with the above formulae and all subsequent formulae, a chemical bond having the symbol "*" represent a free valence of the corresponding structural fragment.

The properties of the agent according to the present invention are particularly advantageous when it is packaged as an aerosol spray, aerosol foam, pump spray, or pump foam. This preferred form of packaging is described later in detail.

Starch is a reserve carbohydrate stored by many plants in the form of large starch grains (granules), usually 1 to 200 µm in size, in various parts of the plant, for example, in tubers or roots, cereal seeds, fruits and in the pith. A nonionic starch modified with propylene oxide that can be used according to the invention can be obtained from the starch of potatoes, corn, rice, peas, acorns, chestnuts, barley, wheat, bananas, sago, millet, sorghum, oats, barley, rye, beans, yams, arrowroot or cassava. Particularly pronounced effects according to the present invention are achieved with nonionic tapioca starch modified with propylene oxide, a nonionic potato starch modified with propylene oxide, or with mixtures of these two starches. Very particularly preferably, the agent according to the present invention contains at least one nonionic potato starch modified with propylene oxide.

Starch belongs to the homoglycan family and is a polycondensation product of D-glucose. Starch is made up of three structurally different polymers of d-glucopyranose, namely amylose, amylopectin, and an intermediate fraction. Higher plants contain 0 to 45 wt % amylose, based on dry substance.

The intermediate fraction, also referred to as "anomalous amylopectin," is structurally intermediate between amylose and amylopectin. Quantitative indications defined in the context of this Application for amylopectin includes the intermediate fraction.

Preferably, the nonionic starch modified with propylene oxide has an amylose content of 25 wt % or less, particularly 20 wt % or less, based on weight of the modified starch. Starch having 17 to 22 wt % amylose and 78 to 83 wt % amylopectin is particularly suitable for achieving the effect according to the present invention.

Amylose is made up of predominantly linear α-1,4-glycosidically linked d-glucose, $M_r$ 50,000 to 150,000. The resulting chains form double helices in the starch.

Amylopectin also contains in addition to the α-1,4 links described for amylose, α-1,6 bonds (in an amount from 4 to 6%) as branching points. The average spacing between the branching points is equal to approximately 12 to 17 glucose units. The molar mass of $10^7$ to $7*10^8$ corresponds to approx. $10^5$ glucose units, making amylopectin one of the largest biopolymers. The branching points are distributed over the molecule in such a way that a bundle structure with relatively short side chains develops. Each double helix is formed by two of these side chains. As a result of the many branching points, amylopectin is relatively easily soluble in water.

"Nonionic starch modified with propylene oxide" according to the present invention is a reaction product of a starch with propylene oxide. A reaction product of this kind includes at least one structural unit of formula (PS)

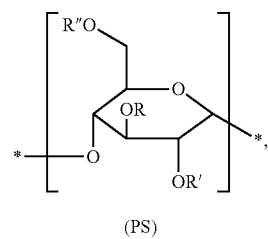

(PS)

wherein at least one of R, R', or R" is a group of the formula

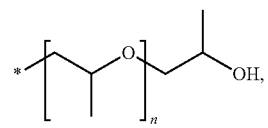

wherein n is greater than or equal to zero, and at most two of R, R', and R" are a hydrogen atom. Nonionic starches modified with propylene oxide are provided, for example, by reacting a natural starch with propylene oxide. Before modification with propylene oxide, the starch can have been exposed to a variety of physical or chemical processes, for example, heat treatment, shear, a thermal, acid-hydrolytic, oxidizing, or enzymatic cleavage, etc.

It is preferred if the nonionic starch modified with propylene oxide is not present in the agent according to the present invention as individual starch grains (granules). Accordingly, the starch grains are disintegrated, for example, by heat or shear, and the corresponding polysaccharide molecules are released from the composite material. The released polysaccharide molecules can be modified with propylene oxide after or before release.

In a preferred embodiment, nonionic starch modified with propylene oxide is gelatinized. When an aqueous suspension of starch is heated or compressed, a tangential swelling of the bodies is then observed at a critical temperature or pressure, with loss of birefringence, a change in X-ray structure, and an abrupt rise in the viscosity of the solution. This phenomenon is called "gelatinization".

Nonionic starches according to the present invention modified with oxide are present in the agent in a molecular weight distribution. Preferred nonionic starches modified with propylene oxide have an average molecular weight from 50 to 2500 kDa (weight average). Molecular weight distribution is determined experimentally by gel filtration chromatography against dextran. The weight average is an average molecular weight that takes into account total weight of the molecules of various molecular weights, and not simply the number of molecules.

For statistical calculation of weight average, firstly the "weight ratio" is defined:

$$w=(N_iM_i)/[\Sigma(N_iM_i)].$$

This indicates the weight proportion, in the sample, of macromolecules that are made up of i segments (e.g., monomer modules) of mass $M_i$ and that occur $N_i$ times in the sample. The weight average of the molecular weight $M_w=\Sigma w_i M_i$ is thus given by $$M_w=[\Sigma(N_iM^2_i)]/[\Sigma(N_iM_i)].$$

In order to adjust the molecular weight, the starch is subjected to mechanical and/or chemical treatment before or after modification with propylene oxide. To elevate the molecular weight, the starch can be crosslinked. Crosslinking of nonionic starch modified with propylene oxide exists when the linear or branched polysaccharide macromolecules of the starch are linked covalently with a crosslinking agent, forming a three-dimensional, insoluble, and still swellable polymeric network. Natural starch is generally considered uncrosslinked, and, if crosslinking were desirable, requires artificial crosslinking by synthesis chemistry. Artificial crosslinking of this kind can be carried out using crosslinking agents. (Nonionic) starches (modified with propylene oxide) that do not exhibit such crosslinking are uncrosslinked.

Crosslinking occurs, for example, using the crosslinking agent epichlorohydrin. Here, a mixture (42-wt % in water) of starch modified with propylene oxide is produced, into which the desired amount of epichlorohydrin is stirred at room temperature. Once target viscosity is reached after a stirring time of 1 to 5 hours with viscosity monitoring, the crosslinked starch is isolated using ordinary methods.

It is particularly preferred, however, if agents according to the present invention contain at least one uncrosslinked nonionic starch modified with propylene oxide.

To achieve a lower molecular weight from 100 to 400 kDa, the starches are preferably exposed to mechanical cleavage, enzymatic cleavage (particularly using α-amylase, β-amylase, glucoamylase, or debranching enzymes), acid-hydrolytic cleavage (particularly using hydrochloric acid, sulfuric acid, or phosphoric acid), thermal cleavage, or a reaction with oxidizing agents (e.g., periodate, hypochlorite, chromic acid, permanganate, nitrogen dioxide, hydrogen peroxide, or organic percarboxylic acid, preferably with hydrogen peroxide). Kneaders, extruders, stator/rotor machines, and/or agitators are suitable for mechanical cleavage of the starch.

Oxidative cleavage using hydrogen peroxide is preferred. Here, for example, the nonionic starch modified with propylene oxide is added to water, heated to 50 to 70° C., hydrogen peroxide is added, and stirring occurs at 70 to 85° C. for 2 to 5 hours.

Propylene oxide content of the starch affects the fine-tuning of the hairstyle hold and hairstyle flexibility, as well as stability of the cosmetic agents. The parameters can be further optimized if the nonionic starch modified with propylene oxide has, based on weight of the modified starch, a propylene oxide content preferably from 1 to 20 wt %, more preferably from 4 to 12 wt %, very preferably from 9.5 to 10.5 wt % or from 4.0 to 6.0 wt %. Propylene oxide content can be determined, for example, by carrying out a Hodges cleavage using the method according to DIN EN 13268.

Those cosmetic agents wherein the nonionic starch modified with propylene oxide has, in a 43-wt % aqueous solution, a preferred viscosity in the range from 150 to 1,500,000 mPa·s (Brookfield viscosimeter, spindle 7 at 20° C. and 20 rpm) are outstandingly suitable for purposes of the invention. Particularly suitable starches modified with propylene oxide have viscosities from 10,000 to 200,000 mPa·s, particularly preferably from 25,000 to 180,000 mPa·s (measured under the conditions recited above).

Nonionic starch modified with propylene oxide that is particularly preferred is uncrosslinked, has an average molecular weight (weight average) from 100 to 2000 kDa, particularly from 500 to 1800 kDa, very preferably from 700 to 1000 kDa, and has a propylene oxide content, based on weight of the modified starch, from 1 to 20 wt %, preferably from 4 to 12 wt %, very preferably from 9.5 to 10.5 wt % or from 4.0 to 6.0 wt %. This is preferably a tapioca starch or potato starch, particularly a potato starch.

Nonionic potato starch modified with propylene oxide that is very particularly preferred according to the present invention is uncrosslinked, has an average molecular weight (weight average) from 100 to 2000 kDa, particularly from 500 to 1800 kDa, very preferably from 700 to 1000 kDa, and has a propylene oxide content, based on weight of the modified potato starch, from 4 to 12 wt %, very preferably from 9.5 to 10.5 wt % or from 4.0 to 6.0 wt %.

It is preferred if the cosmetic agent contains nonionic starch modified with propylene oxide in an amount from 0.1 wt % to 10 wt %, preferably from 0.2 wt % to 5.0 wt %, very preferably from 1.0 to 3.0 wt %, based on weight of the agent.

In addition, the agent according to the present invention contains at least one nonionic film-forming and/or nonionic setting polymer (b). This polymer differs from the nonionic starch modified with propylene oxide. A "nonionic" polymer according to the present invention is a polymer containing, in a protic solvent under standard conditions, substantially no structural units having cationic or anionic groups that must be compensated for by counterions to maintain electroneutrality.

The nonionic film-forming and/or nonionic setting polymers (b) are present in agents according to the present invention preferably in an amount from 0.1 wt % to 20.0 wt %, more preferably from 0.2 wt % to 15.0 wt %, very particularly from 0.5 wt % to 10.0 wt %, based on weight of the agent according to the present invention.

Preferred nonionic film-forming and/or nonionic hair-setting polymers (b) are homo- or copolymers constructed from at least one of the following monomers: N-vinylpyrrolidone, N-vinylcaprolactam, vinyl esters (e.g., vinyl acetate, vinyl alcohol), acrylamide, methacrylamide, alkyl- and dialkylacrylamide (particularly N-methyl- and N,N-dimethylacrylamide), alkyl- and dialkylmethacrylamide (particularly N-methyl- and N,N-dimethylmethacrylamide), alkyl acrylate, alkyl methacrylate, with the alkyl groups of these monomers chosen from ($C_1$ to $C_3$) alkyl groups.

Nonionic polymers based on ethylenically unsaturated monomers and are very particularly suitable for agents according to the present invention contain at least one of the following structural units:

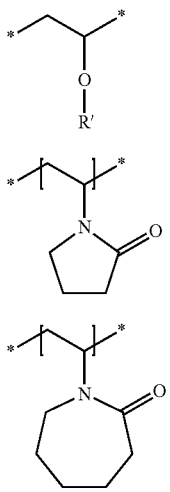

wherein R' is a hydrogen atom or a ($C_1$ to $C_{30}$) acyl group, particularly a hydrogen atom or an acetyl group.

Homopolymers of vinyl caprolactam or of vinylpyrrolidone (such as Luviskol® K 90 or Luviskol® K 85 of the BASF SE company), copolymers of vinylpyrrolidone and vinyl acetate (it being preferred if the molar ratio between the contained structural units of the polymer from the N-vinylpyrrolidone monomer and the contained structural units of the polymer from the vinyl acetate monomer is in the range from 20:80 to 80:20, particularly from 30:70 to 60:40; marketed, for example, under the trademark Luviskol® VA 37, Luviskol® VA 55, Luviskol® VA 64, and Luviskol® VA 73 by the BASF SE company), terpolymers of vinylpyrrolidone, vinyl acetate, and vinyl propionate, polyacrylamides (such as Akypomine® P 191 of the CHEM-Y company), polyvinyl alcohols (marketed, for example, under the commercial names Elvanol® of DuPont or Vinol® 523/540 of the Air Products company), terpolymers of vinylpyrrolidone, methacrylamide, and vinylimidazole (such as Luviset® Clear of the BASF SE company), are particularly suitable.

Agents containing as a nonionic film-forming and/or nonionic setting polymer (b) at least one polymer chosen from
  polyvinylpyrrolidone,
  copolymers of N-vinylpyrrolidone and vinyl esters of carboxylic acids having 2 to 18 carbon atoms, particularly N-vinylpyrrolidone and vinyl acetate,
are very particularly preferred.

The agents of embodiments A) to T) are further considered, in particular, to be very particularly preferred:

A): An agent for treating keratin-containing fibers, particularly human hair, comprising, in a cosmetically acceptable carrier,
(a) at least one uncrosslinked nonionic starch modified with propylene oxide, and
(b) polyvinylpyrrolidone.

B): An agent for treating keratin-containing fibers, particularly human hair, comprising, in a cosmetically acceptable carrier,
(a) at least one uncrosslinked nonionic starch modified with propylene oxide, and
(b) a copolymer manufactured from monomers N-vinylpyrrolidone and vinyl acetate, particularly from no further monomers.

C): A cosmetic agent comprising, in a cosmetically acceptable carrier,
(a) at least one uncrosslinked nonionic potato starch modified with propylene oxide, and
(b) polyvinylpyrrolidone.

D): A cosmetic agent comprising, in a cosmetically acceptable carrier,
(a) at least one uncrosslinked nonionic potato starch modified with propylene oxide, and
(b) a copolymer manufactured from monomers N-vinylpyrrolidone and vinyl acetate, particularly from no further monomers.

E): A cosmetic agent comprising, in a cosmetically acceptable carrier,
(a) at least one uncrosslinked nonionic starch modified with propylene oxide, having a molecular weight (weight average) from 50 to 2500 kDa, preferably 100 to 2000 kDa, more preferably from 500 to 1800 kDa, very preferably from 700 to 1000, and
(b) polyvinylpyrrolidone.

F): A cosmetic agent comprising, in a cosmetically acceptable carrier,
(a) at least one uncrosslinked nonionic starch modified with propylene oxide and having a molecular weight (weight average) from 50 to 2500 kDa, preferably 100 to 2000 kDa, more preferably from 500 to 1800 kDa, very preferably from 700 to 1000, and
(b) a copolymer manufactured from monomers N-vinylpyrrolidone and vinyl acetate, particularly from no further monomers.

G): A cosmetic agent comprising, in a cosmetically acceptable carrier,
(a) at least one uncrosslinked nonionic potato starch modified with propylene oxide, having a molecular weight (weight average) from 50 to 2500 kDa, preferably 100 to 2000 kDa, more preferably from 500 to 1800 kDa, very preferably from 700 to 1000, and
(b) polyvinylpyrrolidone.

H): A cosmetic agent comprising, in a cosmetically acceptable carrier,
(a) at least one uncrosslinked nonionic potato starch modified with propylene oxide and having a molecular weight (weight average) from 50 to 2500 kDa, preferably 100 to 2000 kDa, more preferably from 500 to 1800 kDa, very preferably from 700 to 1000, and
(b) a copolymer manufactured from monomers N-vinylpyrrolidone and vinyl acetate, particularly from no further monomers.

I): A cosmetic agent comprising, in a cosmetically acceptable carrier,
(a) at least one uncrosslinked nonionic starch modified with propylene oxide, having a propylene oxide content from 1 to 20 wt %, preferably from 4 to 12 wt %, more preferably from 9.5 to 10.5 wt % or from 4.0 to 6.0 wt %, based on weight of the modified starch, and
(b) polyvinylpyrrolidone.

J): A cosmetic agent comprising, in a cosmetically acceptable carrier,
(a) at least one uncrosslinked nonionic starch modified with propylene oxide, having a propylene oxide content from 1 to 20 wt %, preferably from 4 to 12 wt %, more preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

K): A cosmetic agent comprising, in a cosmetically acceptable carrier,
(a) at least one uncrosslinked nonionic potato starch modified with propylene oxide, having a propylene oxide content from 1 to 20 wt %, preferably from 4 to 12 wt %, more preferably from 9.5 to 10.5 wt % or from 4.0 to 6.0 wt %, based on weight of the modified starch, and
(b) polyvinylpyrrolidone.

L): A cosmetic agent comprising, in a cosmetically acceptable carrier,
(a) at least one uncrosslinked nonionic potato starch modified with propylene oxide, having a propylene oxide content from 1 to 20 wt %, preferably from 4 to 12 wt %, more preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

M): A cosmetic agent comprising, in a cosmetically acceptable carrier,
(a) at least one uncrosslinked nonionic starch modified with propylene oxide, having a molecular weight (weight average) from 50 to 2500 kDa, preferably 100 to 2000 kDa, more preferably from 500 to 1800 kDa, very preferably from 700 to 1000, and having a propylene oxide content from 1 to 20 wt %, preferably from 4 to 12 wt %, more preferably from 9.5 to 10.5 wt % or from 4.0 to 6.0 wt %, based on weight of the modified starch, and
(b) polyvinylpyrrolidone.

N): A cosmetic agent comprising, in a cosmetically acceptable carrier,
(a) at least one uncrosslinked nonionic starch modified with propylene oxide, having a molecular weight (weight average) from 50 to 2500 kDa, preferably 100 to 2000 kDa, more preferably from 500 to 1800 kDa, very preferably from 700 to 1000, and having a propylene oxide content from 1 to 20 wt %, preferably from 4 to 12 wt %, more preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

O): A cosmetic agent comprising, in a cosmetically acceptable carrier,
(a) at least one uncrosslinked nonionic potato starch modified with propylene oxide, having a molecular weight (weight average) from 50 to 2500 kDa, preferably 100 to 2000 kDa, more preferably from 500 to 1800 kDa, very preferably from 700 to 1000, and having a propylene oxide content from 1 to 20 wt %, preferably from 4 to 12 wt %, more preferably from 9.5 to 10.5 wt % or from 4.0 to 6.0 wt %, based on weight of the modified starch, and
(b) polyvinylpyrrolidone.

P): A cosmetic agent comprising, in a cosmetically acceptable carrier,
(a) at least one uncrosslinked nonionic potato starch modified with propylene oxide, having a molecular weight (weight average) from 50 to 2500 kDa, preferably 100 to 2000 kDa, more preferably from 500 to 1800 kDa, very preferably from 700 to 1000, and having a propylene oxide content from 1 to 20 wt %, preferably from 4 to 12 wt %, more preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

Q): A cosmetic agent comprising, in a cosmetically acceptable carrier,
(a) at least one uncrosslinked nonionic starch modified with propylene oxide, having a molecular weight (weight average) from 500 to 1800 kDa, preferably from 700 to 1000, and having a propylene oxide content from 4 to 12 wt %, more preferably from 9.5 to 10.5 wt % or from 4.0 to 6.0 wt %, based on weight of the modified starch, and
(b) polyvinylpyrrolidone.

R): A cosmetic agent comprising, in a cosmetically acceptable carrier,
(a) at least one uncrosslinked nonionic starch modified with propylene oxide, having a molecular weight (weight average) from 500 to 1800 kDa, preferably from 700 to 1000, and having a propylene oxide content from 4 to 12 wt %, preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

S): A cosmetic agent comprising, in a cosmetically acceptable carrier,
(a) at least one uncrosslinked nonionic potato starch modified with propylene oxide, having a molecular weight (weight average) from 500 to 1800 kDa, preferably from 700 to 1000, and having a propylene oxide content from 4 to 12 wt %, preferably from 9.5 to 10.5 wt % or from 4.0 to 6.0 wt %, based on weight of the modified starch, and
(b) polyvinylpyrrolidone.

T): A cosmetic agent comprising, in a cosmetically acceptable carrier,
(a) at least one uncrosslinked nonionic potato starch modified with propylene oxide and having a molecular weight (weight average) from 500 to 1800 kDa, preferably from 700 to 1000, and having a propylene oxide content from 4 to 12 wt %, preferably from 9.5 to 10.5 wt % or from 4.0 to 6.0 wt %, based on weight of the modified starch, and
(b) a copolymer manufactured from monomers N-vinylpyrrolidone and vinyl acetate, particularly from no further monomers.

The preferred embodiments, in particular the preferred utilization quantities of the above components, apply in embodiments A) to T). Preferred viscosities of the starch modified with propylene oxide are also considered preferred according to embodiments A) to T).

In addition to nonionic film-forming and/or nonionic setting polymers (b) used, agents according to the present invention can have at least one further film-forming and/or setting polymer different from polymer (a) and (b).

To intensify the effect, agents according to the present invention preferably additionally contain at least one surfactant, with nonionic, anionic, cationic, and ampholytic surfactants suitable in principle. The group of ampholytic or amphoteric surfactants includes zwitterionic surfactants and ampholytes. The surfactants can, according to the present invention, already have an emulsifying effect.

The additional surfactants are present in the agent preferably in an amount from 0.01 wt % to 5 wt %, more preferably from 0.05 wt % to 0.5 wt %, based on weight of the agent.

It is particularly preferred if agents according to the present invention additionally contain at least one nonionic surfactant.

Nonionic surfactants contain as a hydrophilic group, for example, a polyol group, a polyalkylene glycol ether group, or a combination of a polyol and polyglycol ether group. Such compounds include:

- addition products of 2 to 100 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group,
- addition products, end-capped with a methyl or $C_2$ to $C_6$ alkyl residue, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as, for example, the grades obtainable under the marketing designations Dehydol® LS, Dehydol® LT (Cognis),
- $C_{12}$ to $C_{30}$ fatty acid mono- and diesters of addition products of 1 to 30 mol ethylene oxide with glycerol,
- addition products of 5 to 60 mol ethylene oxide with castor oil and hardened castor oil,
- polyol fatty acid esters such as the commercial product Hydagen® HSP (Cognis), or Sovermol® grades (Cognis),
- alkoxylated triglycerides,
- alkoxylated fatty acid alkyl esters of formula (E4-I)

$$R^1CO\text{---}(OCH_2CHR^2)_w OR^3 \qquad (\text{E4-I}),$$

wherein $R^1CO$ is a linear or branched, saturated and/or unsaturated acyl residue having 6 to 22 carbon atoms, $R^2$ is hydrogen or methyl, $R^3$ is linear or branched alkyl residues having 1 to 4 carbon atoms, and w is a number from 1 to 20,
- amine oxides,
- hydroxy mixed ethers as described, for example, in German Patent Application No. 19738866,
- sorbitan fatty acid esters and addition products of ethylene oxide with sorbitan fatty acid esters, for example, polysorbates,
- sugar fatty acid esters and addition products of ethylene oxide with sugar fatty acid esters,
- addition products of ethylene oxide with fatty acid alkanolamides and fatty amines,
- sugar surfactants of the alkyl and alkenyl oligoglycoside types, according to formula (E4-II)

$$R^4O\text{-}[G]_p \qquad (\text{E4-II}),$$

wherein $R^4$ is an alkyl or alkenyl residue having 4 to 22 carbon atoms, G is a sugar residue having 5 or 6 carbon atoms, and p is a number from 1 to 10. They can be obtained according to relevant methods of preparative organic chemistry.

Alkylene oxide addition products with saturated linear fatty alcohols and fatty acids, each having 2 to 100 mol ethylene oxide per mol of fatty alcohol or fatty acid, are very particularly preferred nonionic surfactants. Preparations having outstanding properties are likewise obtained when they contain, as nonionic surfactants, $C_{12}$ to $C_{30}$ fatty acid mono- and diesters of addition products of 1 to 30 mol ethylene oxide with glycerol and/or addition products of 5 to 60 mol ethylene oxide with castor oil and hardened castor oil.

Very particularly preferably, agents according to the present invention contain as a surfactant at least one addition product of 15 to 100 mol ethylene oxide, particularly 15 to 50 mol ethylene oxide, with a linear or branched (particularly linear) fatty alcohol having 8 to 22 carbon atoms. This refers very particularly preferably to ceteareth-15, ceteareth-25, or ceteareth-50, marketed as Eumulgin® CS 15 (COGNIS), Cremophor A25 (BASF SE), or Eumulgin® CS 50 (COGNIS).

All anionic surface-active substances suitable for use on the human body are, in principle, appropriate as anionic surfactants. These are characterized by an anionic group imparting water solubility, for example, a carboxylate, sulfate, sulfonate, or phosphate group, and a lipophilic alkyl group having approximately 8 to 30 carbon atoms. Glycol ether or polyglycol ether groups, ester, ether, and amide groups, and hydroxyl groups can additionally be contained in the molecule. Examples of suitable anionic surfactants are, each in the form of the sodium, potassium, and ammonium and mono-, di, and trialkanolammonium salts having 2 to 4 carbon atoms in the alkanol group:

- linear and branched fatty acids having 8 to 30 carbon atoms (soaps);
- ethercarboxylic acids of the formula R—O—(CH$_2$—CH$_2$O)$_x$—CH$_2$—COOH, wherein R is a linear alkyl group having 8 to 30 carbon atoms and x=0 or is 1 to 16;
- acyl sarcosides having 8 to 24 carbon atoms in the acyl group;
- acyl taurides having 8 to 24 carbon atoms in the acyl group;
- acyl isethionates having 8 to 24 carbon atoms in the acyl group;
- sulfosuccinic acid mono- and dialkyl esters having 8 to 24 carbon atoms in the alkyl group, and sulfosuccinic acid monoalkylpolyoxyethyl esters having 8 to 24 carbon atoms in the alkyl group and 1 to 6 oxyethyl groups;
- linear alkanesulfonates having 8 to 24 carbon atoms;
- linear alpha-olefinsulfonates having 8 to 24 carbon atoms;
- alpha-sulfo fatty acid methyl esters of fatty acids having 8 to 30 carbon atoms; alkyl sulfates and alkyl polyglycol ether sulfates of the formula R—O—(CH$_2$—CH$_2$—O)$_x$—OSO$_3$H, wherein R is preferably a linear alkyl group having 8 to 30 carbon atoms and x=0 or is 1 to 12;
- mixtures of surface-active hydroxysulfonates;
- sulfated hydroxyalkylpolyethylene and/or hydroxyalkylenepropylene glycol ethers;
- sulfonates of unsaturated fatty acids having 8 to 24 carbon atoms and 1 to 6 double bonds;
- esters of tartaric acid and citric acid with alcohols, representing addition products of approximately 2 to 15 molecules of ethylene oxide and/or propylene oxide with fatty alcohols having 8 to 22 carbon atoms;
- sulfated fatty acid alkylene glycol esters of formula (E1-II)

$$R^7CO(AlkO)_n SO_3M \qquad (\text{E1-II})$$

wherein $R^7CO$ is a linear or branched, aliphatic, saturated and/or unsaturated acyl residue having 6 to 22 carbon atoms, Alk is CH$_2$CH$_2$, CHCH$_3$CH$_2$, and/or CH$_2$CHCH$_3$, n is a number from 0.5 to 5, and M is a cation, as described in German Patent Application No. 197 36 906;
- amide ethercarboxylic acids;
- condensation products of $C_8$ to $C_{30}$ fatty alcohols with protein hydrolysates and/or amino acids and derivatives thereof, known to one skilled in the art as protein fatty acid condensates, such as the Lamepon® grades, Gluadin® grades, Hostapon® KCG, or the Amisoft® grades.

Preferred anionic surfactants are alkyl sulfates, alkyl polyglycol ether sulfates, and ether carboxylic acids having 10 to 18 carbon atoms in the alkyl group and up to 12 glycol ether groups in the molecule, sulfosuccinic acid mono- and dialkyl esters having 8 to 18 carbon atoms in the alkyl group, and sulfosuccinic acid monoalkylpolyoxyethyl esters having 8 to 18 carbon atoms in the alkyl group and 1 to 6 oxyethyl groups, monoglycerol disulfates, alkyl and alkenyl ether phosphates, as well as protein fatty acid condensates.

Cationic surfactants of the quaternary ammonium compound, esterquat, and amidoamine types are further usable according to the present invention. Preferred quaternary ammonium compounds are ammonium halides, particularly chlorides and bromides (e.g., alkyltrimethylammonium chlorides, dialkyldimethylammonium chlorides, and trialkylmethylammonium chlorides). Long alkyl chains of these surfactants preferably have 10 to 18 carbon atoms (e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride). Further preferred cationic surfactants are the imidazolium compounds known by the INCI names Quaternium-27 and Quaternium-83.

"Zwitterionic surfactants" are those surface-active compounds having in the molecule at least one quaternary ammonium group and at least one —$COO^{(-)}$ or $SO_3^{(-)}$ group. Particularly suitable zwitterionic surfactants are betaines, such as the N-alkyl-N,N-dimethylammonium glycinates (e.g., cocalkyldimethylammonium glycinate), N-acylaminopropyl-N,N-dimethylammonium glycinates (e.g., cocacylaminopropyldimethylammonium glycinate), and 2-alkyl-3-carboxymethyl-3-hydroxyethylimidazolines, each having 8 to 18 carbon atoms in the alkyl or acyl group, as well as cocacylaminoethylhydroxyethylcarboxymethyl glycinate. A preferred zwitterionic surfactant is the fatty acid amide derivative known by the INCI name Cocamidopropyl Betaine.

"Ampholytes" are those surface-active compounds having in the molecule, in addition to a $C_8$ to $C_{24}$ alkyl or acyl group, at least one free amino group and at least one —COOH or —$SO_3H$ group, and are capable of forming internal salts. Examples of suitable ampholytes are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, each having approximately 8 to 24 carbon atoms in the alkyl group. Particularly preferred ampholytes are N-cocalkylaminopropionate, cocacylaminoethylaminopropionate, and $C_{12}$ to $C_{18}$ acyl sarcosine.

Agents according to the present invention contain the ingredients or active substances in a cosmetically acceptable carrier.

Preferred cosmetically acceptable carriers are aqueous, alcoholic, or aqueous alcoholic media preferably having at least 10 wt % water, based on total agent. The alcohols used can be, in particular, lower alcohols having 1 to 4 carbon atoms usually used for cosmetic purposes (e.g., ethanol and isopropanol). It is preferred to use at least one ($C_1$ to $C_4$) monoalkyl alcohol in the agents, particularly in an amount from 1 to 50 wt %, more particularly from 5 to 30 wt %. This is particularly preferred for packaging as a pump foam or aerosol foam.

Organic solvents or a mixture of solvents having a boiling point of 400° C. or less can be contained as additional co-solvents in an amount from 0.1 to 15 wt %, preferably from 1 to 10 wt % based on total agent. Unbranched or branched hydrocarbons such as pentane, hexane, isopentane, and cyclic hydrocarbons such as cyclopentane and cyclohexane are particularly suitable as additional co-solvents. Further particularly preferred water-soluble solvents are glycerol, ethylene glycol, and propylene glycol, in an amount of up to 30 wt % based on total agent.

The addition in particular of glycerol and/or propylene glycol and/or polyethylene glycol and/or polypropylene glycol increases the flexibility of the polymer film formed when the agent according to the present invention is used. If a flexible hold is desired, the agents preferably contain 0.01 to 30 wt % glycerol and/or propylene glycol and/or polyethylene glycol and/or polypropylene glycol, based on total agent.

The agents preferably have a pH from 2 to 11. Particularly preferably, the pH range is from 2 to 8. Reference to pH here, for purposes of this document, is to pH at 25° C. unless otherwise noted.

Agents according to the present invention can also contain adjuvants and additives usually added to conventional styling agents.

Additional care-providing substances can be particularly recited as suitable adjuvants and additives.

Silicone oil and/or a silicone gum can be used, for example, as a care-providing substance.

Silicone oils or silicone gums suitable according to the present invention are, in particular, dialkyl- and alkylarylsiloxanes (e.g., dimethylpolysiloxane and methylphenylsiloxane), as well as alkoxylated, quaternized, or also anionic derivatives thereof. Cyclic and linear polydialkylsiloxanes, alkoxylated and/or aminated derivatives thereof, dihydroxypolydimethylsiloxanes, and polyphenylalkylsiloxanes are preferred.

Silicone oils produce a very wide variety of effects. For example, they simultaneously influence dry and wet combability, the feel of dry and wet hair, and shine. The skilled artisan understands "silicone oils" to mean several structures of organosilicon compounds. They are understood firstly as dimethiconols. The following commercial products are examples of such products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401DC (all Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both Guardian Laboratories), Nonychosine E, Nonychosine V (both Exsymol), SanSurf Petrolatum-25, Satin Finish (both Collaborative Laboratories, Inc.), Silatex-D30 (Cosmetic Ingredient Resources), Silsoft 148, Silsoft E-50, Silsoft E-623 (all Crompton Corporation), SM555, SM2725, SM2765, SM2785 (all GE Silicones), Taylor T-Sil CD-1, Taylor TME-4050E (all Taylor Chemical Company), TH V 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all Wacker-Chemie GmbH).

Dimethicones are the second group of silicones that can be present according to the present invention. They can be linear and branched, and also cyclic or cyclic and branched.

Dimethicone copolyols (S3) are a further group of suitable silicones. Corresponding dimethicone copolyols are commercially obtainable and marketed, for example, by the Dow Corning company under the designation Dow Corning® 5330 Fluid.

The teaching of the present invention also includes the fact that dimethiconols, dimethicones, and/or dimethicone copolymers can already be present as an emulsion. The corresponding emulsion of dimethiconols, dimethicones, and/or dimethicone copolyols can be manufactured both after manufacture of the corresponding dimethiconols, dimethicones, and/or dimethicone copolyols, from them and using usual emulsification methods known to the skilled artisan. For this purpose, cationic, anionic, nonionic, or zwitterionic surfactants and emulsifiers can be used as auxiliaries, as adjuvants for manufacture of the corresponding emulsions. The emulsions of dimethiconols, dimethicones, and/or dimethicone copolyols can also be manufactured directly by an emulsion polymerization method. Such methods are also very familiar to the skilled artisan.

If the dimethiconols, dimethicones, and/or dimethicone copolyols are used as an emulsion, the droplet size of the emulsified particles is then, according to the present invention, from 0.01 to 10,000 µm, preferably 0.01 to 100 µm, more preferably 0.01 to 20 µm, and very preferably 0.01 to 10 µm. Particle size is determined using the light-scattering method.

If branched dimethiconols, dimethicones, and/or dimethicone copolyols are used, then the branching is greater than a branching that occurs randomly as a result of contaminants in the respective monomers. "Branched" dimethiconols, dimethicones, and/or dimethicone copolyols, for purposes of the present invention, mean that the degree of branching is 0.01% or greater. A degree of branching 0.1% or greater is preferred, and very particularly preferably it is 0.5% or greater. The degree of branching is determined from the ratio of unbranched monomers to branching monomers (i.e., to the quantity of tri- and tetrafunctional siloxanes). Low-branching and high-branching dimethiconols, dimethicones, and/or dimethicone copolyols can be very particularly preferred according to the present invention.

Particularly preferred silicones are aminofunctional silicones, particularly those silicones grouped under the INCI name Amodimethicones. It is therefore preferred if the agents additionally contain at least one aminofunctional silicone. These are silicones having at least one optionally substituted amino group. These silicones are referred to according to the INCI declaration as Amodimethicones, and are obtainable, for example, in the form of an emulsion, as a commercial product Dow Corning® 939 or as a commercial product Dow Corning® 949, mixed with a cationic and a nonionic surfactant.

Those aminofunctional silicones having an amine number of 0.25 meq/g or greater, preferably 0.3 meq/g or greater, and very preferably 0.4 meq/g or greater are preferably used. The amine number is the milliequivalent of amine per gram of aminofunctional silicone. It can be ascertained by titration, and can also be indicated with the "mg KOH/g" unit.

The agents contain silicones preferably in amounts from 0.01 wt % to 15 wt %, more preferably from 0.05 to 2 wt %, based on total agent.

The agent can contain as a care-providing substance of a different compound class, for example, at least one protein hydrolysate and/or a derivative thereof.

Protein hydrolysates are product mixtures obtained by acid-, base-, or enzyme-catalyzed breakdown of proteins. "Protein hydrolysates" according to the present invention also means total hydrolysates as well as individual amino acids and derivatives thereof, and mixtures of different amino acids. The molecular weight of protein hydrolysates usable according to the present invention is from 75 (the molecular weight of glycine) to 200,000; the molecular weight is preferably 75 to 50,000 Dalton, and very particularly preferably to 75 to 20,000 Dalton.

According to the present invention, protein hydrolysates of vegetable, animal, marine or synthetic origin can be used.

Animal protein hydrolysates include protein hydrolysates of elastin, collagen, keratin, silk, and milk protein, which can also be present in the form of salts. Such products are marketed, for example, under the trademarks Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm), and Kerasol® (Croda).

Protein hydrolysates are present in agents according to the present invention, for example, in concentrations from 0.01 wt % to 20 wt %, preferably from 0.05 wt % to 15 wt %, and very preferably in amounts from 0.05 wt % to 5 wt %, based on total application preparation.

The agent according to the present invention can further contain at least one vitamin, provitamin, vitamin precursor, and/or derivative thereof as a care-providing substance.

Those vitamins, provitamins, and vitamin precursors usually assigned to groups A, B, C, E, F, and H are preferred according to the present invention.

The substances referred to as "vitamin A" includes retinol (vitamin $A_1$) as well as 3,4-didehydroretinol (vitamin $A_2$). β-Carotene is the provitamin of retinol. Vitamin A components that are appropriate according to the present invention include vitamin A acid and its esters, vitamin A aldehyde, and vitamin A alcohol, as well as esters thereof such as palmitate and acetate. The agents contain the vitamin A component preferably in amounts from 0.05 to 1 wt % based on total application preparation.

Members of the vitamin B group or vitamin B complex are, among others, vitamin $B_1$ (thiamine), vitamin $B_2$ (riboflavin), vitamin $B_3$ (nicotinic acid and/or nicotinic acid amide (niacinamide)), vitamin $B_5$ (pantothenic acid, panthenol, and pantolactone), vitamin $B_6$ (pyroxidine as well as pyridoxamine and pyridoxal), vitamin C (ascorbic acid), vitamin E (tocopherols, particularly α-tocopherol), vitamin F (linoleic acid and/or linolenic acid), vitamin H.

Agents according to the present invention preferably contain vitamins, provitamins, and vitamin precursors from groups A, B, C, E and H. Panthenol, pantolactone, pyridoxine and its derivatives, as well as nicotinic acid amide and biotin, are particularly preferred.

D-panthenol is very particularly preferably used as a care-providing substance, optionally in combination with at least one of the silicone derivatives recited above.

Like the addition of glycerol and/or propylene glycol, the addition of panthenol also increases the flexibility of the polymer film formed upon utilization of the agent according to the present invention. If a particularly flexible hold is desired, the agents can contain panthenol instead of or in addition to glycerol and/or propylene glycol. In a preferred embodiment, the agents contain panthenol, preferably in an amount from 0.05 to 10 wt %, more preferably 0.1 to 5 wt %, based on total agent.

The agents according to the present invention can further contain at least one plant extract as a care-providing substance.

These extracts are usually produced by extraction of the entire plant. In individual cases, however, it may also be preferred to produce the extracts exclusively from blossoms and/or leaves of the plant.

According to the present invention, preferred extracts are from green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root.

It may also be preferred to use mixtures of several, particularly two different plant extracts in the agents.

Mono- and/or oligosaccharides can also be used as a care-providing substance in agents according to the present invention.

Both monosaccharides and oligosaccharides, for example, raw sugar, milk sugar, and raffinose, can be used. Use of monosaccharides is preferred. Among the monosaccharides, those compounds having 5 or 6 carbon atoms are preferred.

Suitable pentoses and hexoses include ribose, arabinose, xylose, lyxose, allose, altrose, glucose, mannose, gulose, idose, galactose, talose, fucose and fructose. Arabinose, glucose, galactose and fructose are carbohydrates that are preferably used. It is very particularly preferred to use glucose, which is suitable both in the D-(+) or L-(−) configuration or as a racemate. Derivatives of these pentoses and hexoses, such as the corresponding -onic and -uronic acids (sugar acids), sugar alcohols, and glycosides, can also be used according to the present invention. Preferred sugar acids are gluconic acid, glucuronic acid, saccharic acid, mannosaccharic acid, and mucic acid. Preferred sugar alcohols are sorbitol, mannitol, and dulcitol. Preferred glycosides are the methylglucosides. Because the mono- or oligosaccharides that are used are usually obtained from natural raw materials such as starch, they exhibit the configurations corresponding to those raw materials (e.g., D-glucose, D-fructose and D-galactose).

The mono- or oligosaccharides are present in agents according to the present invention preferably in an amount from 0.1 to 8 wt %, more preferably from 1 to 5 wt %, based on total application preparation.

The agent can furthermore contain at least one lipid as a care-providing substance.

Lipids suitable according to the present invention are phospholipids (e.g., soy lecithin, egg lecithin, and kephalins), as well as substances known by the INCI names Linoleamidopropyl PG-Dimonium Chloride Phosphate, Cocamidopropyl PG-Dimonium Chloride Phosphate, and Stearamidopropyl PG-Dimonium Chloride Phosphate. These are marketed, for example, by the Mona Company under the commercial designations Phospholipid EFA®, Phospholipid PTC®, and Phospholipid SV®. The agents contain the lipids preferably in amounts from 0.01 to 10 wt %, particularly 0.1 to 5 wt %, based on total application preparation.

Oily substances are also suitable as a care-providing substance.

Included among the natural and synthetic cosmetic oily substances are, for example:

Vegetable oils. Examples of such oils are sunflower oil, olive oil, soybean oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of from 12 to 36 carbon atoms, particularly 12 to 24 carbon atoms, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as di-tert-butyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (Cetiol® S) and di-n-octyl ether (Cetiol® OE), available as commercial products, can be preferred.

Ester oils. "Ester oils" are the esters of $C_6$ to $C_{30}$ fatty acids with $C_2$ to $C_{30}$ fatty alcohols. Monoesters of the fatty acids with alcohols having 2 to 24 carbon atoms are preferred. Particularly preferred are isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

Dicarboxylic acid esters such as di-n-butyl adipate, di-(2-ethylhexyl)adipate, di-(2-ethylhexyl)succinate, and diisotridecyl acelaate, as well as diol esters such as ethylene glycol dioleate, ethylene glycol diisotridecanoate, propylene glycol di-(2-ethylhexanoate), propylene glycol diisostearate, propylene glycol dipelargonate, butanediol diisostearate, neopentyl glycol dicaprylate.

Symmetrical, asymmetrical, or cyclic esters of carbonic acid with fatty alcohols, as described in German Patent Application No. 197 56 454, glycerol carbonate, or dicaprylyl carbonate (Cetiol® CC).

Fatty acid triesters of saturated and/or unsaturated linear and/or branched fatty acids with glycerol.

Fatty acid partial glycerides, which include monoglycerides, diglycerides, and industrial mixtures thereof. When industrial products are used, small quantities of triglycerides may still be present for manufacturing-related reasons. The partial glycerides preferably conform to formula (D4-I):

wherein $R^1$, $R^2$ and $R^3$ are, mutually independently, hydrogen or a linear or branched, saturated and/or unsaturated acyl residue having 6 to 22, preferably 12 to 18 carbon atoms, with the provision that at least one of $R^1$, $R^2$ and $R^3$ is an acyl residue and at least one is hydrogen. The sum (m+n+q) is 0 or a number from 1 to 100, preferably 0 or 5 to 25. Preferably $R^1$ is an acyl residue and $R^2$ and $R^3$ are hydrogen, and the sum (m+n+q) is 0. Typical examples are mono- and/or diglycerides based on hexanoic acid, octanoic acid, 2-ethylhexanoic acid, decanoic acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachidic acid, gadoleic acid, behenic acid and erucic acid, as well as industrial mixtures thereof. Oleic acid monoglycerides are preferably used.

The amount of natural and synthetic cosmetic oily substances used in agents according to the present invention is typically 0.1 to 30 wt %, based on total application preparation, preferably 0.1 to 20 wt %, and particularly 0.1 to 15 wt %.

Although each of the above care-providing substances already yields a satisfactory result by itself, all embodiments wherein the agent contains multiple care-providing substances, including from different groups, are also included within the scope of the present invention.

The addition of a UV filter allows both the preparations and the treated fibers to be protected from damaging influences of UV radiation. At least one UV filter is therefore preferably added to cosmetic agents according to the present invention. Suitable UV filters are not subject to any general restrictions regarding structure and physical properties. Instead, all UV filters usable in the cosmetics sector whose absorption maximum lies in the UVA (315 to 400 nm), UVB (280 to 315 nm), or UVC (<280 nm) regions are suitable. UV filters having an absorption maximum in the UVB region, particularly in the region from approximately 280 to approximately 300 nm, are particularly preferred.

Preferred UV filters include substituted benzophenones, p-aminobenzoic acid esters, diphenylacrylic acid esters, cinnamic acid esters, salicylic acid esters, benzimidazoles, and o-aminobenzoic acid esters.

Examples of usable UV filters are 4-aminobenzoic acid, N,N,N-trimethyl-4-(2-oxoborn-3-ylidenemethyl)aniline methylsulfate, 3,3,5-trimethylcyclohexyl salicylate (Homosalate), 2-hydroxy-4-methoxybenzophenone, 2-phenylbenzimidazole-5-sulfonic acid and potassium, sodium, and triethanolamine salts thereof, 3,3'-(1,4-phenylenedimethylene)-bis(7,7-dimethyl-2-oxo-bicyclo-[2.2.1]hept-1-yl-methanesulfonic acid) and salts thereof, 1-(4-tert-butylphenyl)-3-(4-methoxyphenyl)propane-1,3-dione, α-(2-oxoborn-3-ylidene)toluene-4-sulfonic acid and salts thereof, ethoxylated 4-aminobenzoic acid ethyl ester (PEG-25 PABA; Uvinul® P 25), 4-dimethylaminobenzoic acid 2-ethylhexyl ester, salicylic acid 2-ethylhexyl ester, 4-methoxycinnannic acid isopentyl ester, 4-methoxycinnamic acid 2-ethylhexyl ester, 2-hydroxy-4-methoxybenzophenone-5-sulfonic acid and the sodium salt thereof (Benzophenone-4; Uvinul® MS 40; Uvasorb® S 5), 3-(4'-methylbenzylidene) D,L-camphor, 3-benzylidene camphor (3-Benzylidene Camphor), 4-isopropylbenzylsalicylate, 2,4, 6-trianilino-(p-carbo-2'-ethylhexyl-1'-oxi)-1,3,5-triazine, 3-imidazol-4-ylacrylic acid and ethyl esters thereof, polymers of N-{(2 and 4)-[2-oxoborn-3-ylidenemethyl]benzyl}acrylamide, 2,4-dihydroxybenzophenone, 1,1'-diphenylacrylonitrilic acid 2-ethylhexyl ester, o-aminobenzoic acid menthyl ester, 2,2',4,4'-tetrahydroxybenzophenone, 2,2'-dihydroxy-4,4'-dimethoxybenzophenone, 2,2'-dihydroxy-4,4'-dimethoxybenzophenone-5-sodiumsulfonate, and 2-cyano-3,3-diphenylacrylic acid 2'-ethylhexyl ester. 2-Hydroxy-4-methoxy-benzophenone-5-sulfonic acid and the sodium salt thereof, and/or ethoxylated 4-aminobenozic acid ethyl ester, are preferred.

The UV filters are present usually in amounts from 0.01 to 5 wt %, based on total application preparation. Quantities from 0.1 to 2.5 wt % are preferred.

In a particular embodiment, the cosmetic agent according to the present invention also contains one or more substantive dyes. This allows keratinic fibers treated using the agent to be not only temporarily structured, but at the same time also dyed. This can be particularly desirable when only a temporary coloration is desired, for example, with conspicuous "fashion" colors which can be removed from the keratinic fibers simply by washing.

Substantive dyes are usually nitrophenylenediamines, nitroaminophenols, azo dyes, anthraquinones, or indophenols. Preferred substantive dyes are compounds known by the international designations or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-1-hydroxy-4-nitrobenzene. It is preferred to use cationic substantive dyes. Particularly preferred in this context are (a) cationic triphenylmethane dyes such as Basic Blue 7, Basic Blue 26, Basic Violet 2, and Basic Violet 14;
(b) aromatic systems substituted with a quaternary nitrogen group, such as Basic Yellow 57, Basic Red 76, Basic Blue 99, Basic Brown 16, and Basic Brown 17; and
(c) substantive dyes containing a heterocycle which has at least one quaternary nitrogen atom, such as those recited in European Patent Application 0 998 908, particularly its Claims 6 to 11.

Dyes also known by the designations Basic Yellow 87, Basic Orange 31, and Basic Red 51 are very particularly preferred cationic substantive dyes of group (c). Cationic substantive dyes marketed under the trademark Arianor® are likewise very particularly preferred cationic substantive dyes according to the present invention.

Agents according to this embodiment contain substantive dyes preferably in an amount from 0.001 to 20 wt %, based on total agent.

Preferably, agents according to the present invention are free of oxidizing dye precursor products. Oxidizing dye precursor products are divided into developer components and coupler components. The developer components form the actual dyes with one another under the influence of oxidizing agents or atmospheric oxygen, or by coupling with one or more coupler components.

Agents according to the present invention can be formulated in any form usual for styling agents, for example, as solutions that can be applied onto the hair as a hair lotion or as a pump or aerosol spray, in the form of creams, emulsions, waxes, gels, or also surfactant-containing foaming solutions or other preparations suitable for application to the hair.

Hair creams and hair gels generally contain structuring agents and/or thickening polymers which impart the desired consistency to the products. Structuring agents and/or thickening polymers are used typically in an amount from 0.1 to 10 wt %, based on total product. Quantities from 0.5 to 5 wt %, particularly 0.5 to 3 wt %, are preferred.

Agents according to the present invention are preferably packaged as a pump spray, aerosol spray, pump foam, or aerosol foam.

For this, the agents are packaged in a delivery apparatus that is either a pressurized-gas container additionally filled with propellant ("aerosol container") or a non-aerosol container.

Pressurized-gas containers from which a product is distributed through a valve due to the internal gas pressure of the container are referred to as "aerosol containers." A "non-aerosol container", conversely to the "aerosol" definition, is a vessel under standard pressure from which a product is distributed by mechanical action using a pump system.

Agents according to the present invention are packaged particularly preferably as an aerosol hair foam or aerosol hair spray. The agent therefore preferably also contains at least one propellant. This applies preferably to embodiments A) to T) described above.

Suitable propellants according to the present invention include N2O, dimethyl ether, CO2, air, alkanes having 3 to 5 carbon atoms such as propane, n-butane, isobutane, n-pentane, and isopentane, and mixtures thereof. Dimethyl ether, propane, n-butane, isobutane, and mixtures thereof are preferred.

In a preferred embodiment, the above alkanes, mixtures of those alkanes, or mixtures of those alkanes with dimethyl ether are used as the only propellant. The invention also expressly includes, however, concurrent use of chlorofluorocarbon propellants, particularly fluorocarbons.

For a given spray apparatus, the size of aerosol droplets or foam bubbles and the respective size distribution can be adjusted using the quantitative ratio between the propellant and other ingredients of the preparations.

The amount of propellant used varies based on the specific composition of the agent, the packaging used, and the desired type of product (e.g., hair spray or hair foam). When conventional spray apparatuses are used, aerosol foam products contain propellant preferably in amounts from 1 to 35 wt %, based on total product. Quantities from 2 to 30 wt %, particularly 3 to 15 wt %, are particularly preferred. Aerosol sprays generally contain larger quantities of propellant. Here, the propellant is preferably used in an amount from 30 to 98 wt %, based on total product. Quantities from 40 to 95 wt %, particularly from 50 to 95 wt %, are preferred.

The aerosol products can be manufactured in usual fashion. All ingredients of the particular agent except the propellant are introduced into a suitable pressure-tight container. The latter is then sealed with a valve. Lastly, the desired amount of propellant is introduced using conventional techniques.

Isopentane is preferably suitable as a propellant for foaming gel-type agents in a two-chamber aerosol container, with the propellant incorporated into agents according to the present invention and packaged in the first chamber of the two-chamber aerosol container. In the second chamber of the two-chamber aerosol container is at least one further propellant different from isopentane that builds up in the two-chamber aerosol container a higher pressure than the isopentane. Propellants of the second chamber are preferably chosen from N2O, dimethyl ether, CO2, air, alkanes having 3 or 4 carbon atoms (such as propane, n-butane, isobutane), and mixtures thereof.

Preferred agents according to the present invention and propellants of the aerosol hair foam or aerosol hair spray, as well as the respective amounts of propellant, correspond to the statements already made above.

A second subject of the invention is the use of agents according to the present invention for temporary deformation of hair and/or for hair care.

Agents according to the present invention and products containing these agents, particularly aerosol hair foams or aerosol hair sprays, impart a very strong, durable hairstyle hold to the treated hair even though the hair remains flexible. If the agent is packaged as hair foam, a stable, fine-pored, and creamy foam forms which can be distributed onto hair evenly and without dripping.

A third subject of the invention is a method for treating keratin-containing fibers, particularly human hair, wherein, using a delivery apparatus, an agent according to the first subject of the invention is foamed into foam and the resulting foam is applied onto the keratin-containing fibers.

Preferably, a shape is imparted to the keratin-containing fibers and that shape is fixed in place by the agent of the first subject of the invention.

Those discharge apparatuses recited earlier (see above) are considered preferred according to the present invention.

A fourth subject of the invention is a method for treating keratin-containing fibers, particularly human hair, wherein, using a delivery apparatus, an agent according to the first subject of the invention is applied as a spray onto the keratin-containing fibers.

Preferably, a shape is imparted to the keratin-containing fibers and that shape is fixed in place by the agent of the first subject of the invention.

Those discharge apparatuses recited earlier (see above) are considered preferred according to the present invention.

The Examples that follow are intended to explain the subject matter of the present invention without in any way limiting it.

EXAMPLES

Unless otherwise noted, the quantitative indications below are percentages by weight. The following formulations were produced by mixing the raw materials indicated:

| Raw materials | A | B | C | D | E | F | G | H |
|---|---|---|---|---|---|---|---|---|
| HPS 1[1] | 4.0 | 5.0 | — | — | 6.0 | 3.5 | 5.5 | 4.5 |
| HPS 2[1] | — | — | 4.5 | 3.0 | — | — | — | 2.0 |
| Polyvinylpyrrolidone | 3.5 | — | 3.0 | — | 0.5 | — | 1.0 | 4.0 |
| PVP/VA[3] | — | 5.0 | — | 5.0 | — | 4.5 | 4.0 | — |
| PEG-40 Hydrogenated Castor Oil | 0.1 | 0.1 | 0.1 | 0.1 | 0.1 | 0.1 | 0.1 | 0.1 |
| Cetyltrimethylammonium chloride | 0.1 | 0.1 | 0.1 | 0.1 | 0.1 | 0.1 | 0.1 | 0.1 |
| Ethanol | — | 5.0 | — | 10.0 | — | — | — | 7.5 |
| Water | to 100 | | | | | | | |

[1] Nonionic potato starch modified with propylene oxide (propylene oxide content: 10.0 wt %; viscosity: 64,000 mPa · s; weight average range: 700 to 900 kDa)
[2] Nonionic potato starch modified with propylene oxide (propylene oxide content: 5.0 wt %; viscosity: 128,000 mPa · s; weight average range: 700 to 900 kDa)
[3] Copolymer of N-vinylpyrrolidone and vinyl acetate.

Formulations A to H were each placed into an aerosol container that meets the following technical parameters: aluminum reservoir container with valve (product 522983 PV10697 of the Precision company (Deutsche Präzisions-Ventil GmbH).

The aerosol container was filled with a propellant gas mixture of propane/butane (47 wt % propane, 50 wt % butane, 3 wt % isobutane), yielding a weight ratio of formulation to propellant gas of 92 to 8.

All the formulations produced, after use on the hair, an increase in volume as well as an outstandingly flexible hairstyle hold. The hair received very good care. The formulations were applied in the form of high-volume aerosol foam that breaks significantly only while being used on the hair.

We claim:

1. Agent for treating keratin-containing fibers comprising, in a cosmetically acceptable carrier:
   at least one nonionic starch modified with propylene oxide, and
   at least one nonionic film-forming and/or nonionic setting polymer having at least one structural unit chosen from the structural units of formulae (M1) to (M6),

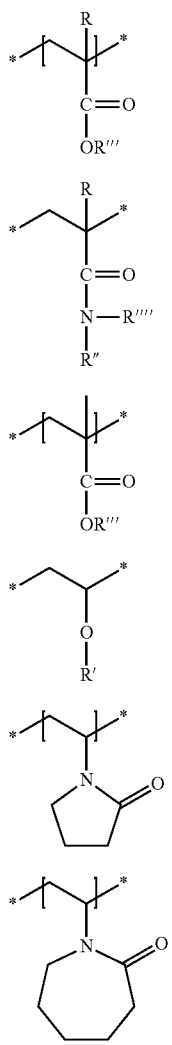

wherein
R is a hydrogen atom or a methyl group,
R' is a hydrogen atom or a ($C_1$ to $C_4$) acyl group,
R" and R"" are, mutually independently, a ($C_1$ to $C_7$) alkyl group or a hydrogen atom,
R'" is a linear or branched ($C_1$ to $C_4$) alkyl group or a ($C_2$ to $C_4$) hydroxyalkyl group;
   wherein the modified nonionic starch has an average molecular weight (weight average) of 100 to 2000 kDa; and
   wherein the modified nonionic starch has a propylene oxide content of 1 to 20 wt %, based on weight of the modified starch.

2. Agent according to claim 1, wherein the modified nonionic starch is a nonionic tapioca starch modified with propylene oxide, a nonionic potato starch modified with propylene oxide, or a mixture thereof.

3. Agent according to claim 1, wherein the modified nonionic starch is present in an amount from 0.1 wt % to 10 wt %, based on weight of the agent.

4. Agent according to claim 1, wherein the modified nonionic starch has, in a 43-wt % aqueous solution, a viscosity in the range from 150 to 1,500,000 mPa·s, based on Brookfield viscosimeter, spindle 7 at 20° C. and 20 rpm.

5. Agent according to claim 1, wherein the modified nonionic starch is at least one uncrosslinked nonionic starch modified with propylene oxide.

6. Agent according to claim 1, wherein the nonionic film-forming and/or nonionic setting polymers (b) are present in an amount from 0.1 wt % to 20.0 wt %, based on weight of the agent.

7. Agent according to claim 1, wherein the nonionic film-forming and/or nonionic setting polymer is at least one polymer chosen from:
   polyvinylpyrrolidone, and
   copolymers of N-vinylpyrrolidone and vinyl esters of carboxylic acids having 2 to 18 carbon atoms.

8. Agent according to claim 1, wherein the agent is in the form of an aerosol foam or aerosol spray.

9. Method for treating keratin-containing fibers comprising foaming an agent according to claim 1 with the use of a delivery apparatus into foam, and applying the resulting foam onto the keratin-containing fibers.

10. Method for treating keratin-containing fibers comprising applying with the use of a delivery apparatus an agent according to claim 1 as a spray onto the keratin-containing fibers.

11. Agent according to claim 1, wherein the viscosity is 25,000 to 180,000 mPa·s.

12. Agent according to claim 1, wherein the molecular weight (weight average) is 500 to 1800 kDa.

13. Agent according to claim 12, wherein the molecular weight (weight average) is 700 to 1000 kDa.

14. Agent according to claim 1, wherein the propylene oxide content is 4 to 12 wt %.

15. Agent according to claim 14, wherein the propylene oxide content is 9.5 to 10.5 wt %.

* * * * *